US012594317B2

(12) United States Patent
Lin

(10) Patent No.: US 12,594,317 B2
(45) Date of Patent: Apr. 7, 2026

(54) TRADITIONAL CHINESE MEDICINE COMPOSITION FOR TREATING NOVEL CORONAVIRUS PNEUMONIA, PREPARATION METHOD, DETECTION METHOD, AND USE THEREOF

(71) Applicant: BEIJING HANDIAN PHARMACEUTICAL CO., LTD., Beijing (CN)

(72) Inventor: Deliang Lin, Beijing (CN)

(73) Assignee: BEIJING HANDIAN PHARMACEUTICAL CO., LTD., Beijing (CN)

( * ) Notice: Subject to any disclaimer, the term of this patent is extended or adjusted under 35 U.S.C. 154(b) by 757 days.

(21) Appl. No.: 17/924,398

(22) PCT Filed: Nov. 13, 2020

(86) PCT No.: PCT/CN2020/128753
§ 371 (c)(1),
(2) Date: Dec. 2, 2022

(87) PCT Pub. No.: WO2021/223397
PCT Pub. Date: Nov. 11, 2021

(65) Prior Publication Data
US 2023/0181666 A1 Jun. 15, 2023

(30) Foreign Application Priority Data

May 8, 2020 (CN) .......................... 202010384148.5

(51) Int. Cl.
*A61K 36/752* (2006.01)
*A61K 9/16* (2006.01)
(Continued)

(52) U.S. Cl.
CPC .......... *A61K 36/752* (2013.01); *A61K 9/1652* (2013.01); *A61K 36/284* (2013.01);
(Continued)

(58) Field of Classification Search
CPC .. A61K 36/752; A61K 9/1652; A61K 36/284; A61K 36/484; A61K 36/532;
(Continued)

(56) References Cited

FOREIGN PATENT DOCUMENTS

| CN | 1456292 A | 11/2003 |
| CN | 1843442 A | 10/2006 |

(Continued)

OTHER PUBLICATIONS

American Dragon, Herb Formulas, 2017, pp. 1-7. (Year: 2017).*

(Continued)

*Primary Examiner* — Trevor Love
(74) *Attorney, Agent, or Firm* — Dobrusin Law Firm, P.C.

(57) ABSTRACT

Provided in the present disclosure are a traditional Chinese medicine composition for treating novel coronavirus pneumonia, a preparation method, a detection method, and the use thereof. The traditional Chinese medicine composition is mainly prepared from the following raw materials in parts by weight: 250-400 parts of *Citri reticulatae pericarpium*, 100-200 parts of *Atractylodis rhizoma*, 100-200 parts of *Magnoliae officinalis cortex*, 200-300 parts of *Glycyrrhizae radix* et *rhizoma*, 200-300 parts of *Agastache rugosus*, 200-300 parts of *Acori tatarinowii rhizoma*, 250-330 parts of *Jujubae fructus*, and 100-200 parts of *Zingiberis rhizoma recens*. Further provided in the present disclosure are a preparation method and a detection method for the traditional Chinese medicine composition.

4 Claims, 3 Drawing Sheets

(51) Int. Cl.

| | |
|---|---|
| *A61K 36/284* | (2006.01) |
| *A61K 36/484* | (2006.01) |
| *A61K 36/532* | (2006.01) |
| *A61K 36/575* | (2006.01) |
| *A61K 36/725* | (2006.01) |
| *A61K 36/882* | (2006.01) |
| *A61K 36/9068* | (2006.01) |
| *A61P 11/00* | (2006.01) |
| *A61P 31/14* | (2006.01) |

(52) U.S. Cl.
CPC .......... *A61K 36/484* (2013.01); *A61K 36/532* (2013.01); *A61K 36/575* (2013.01); *A61K 36/725* (2013.01); *A61K 36/882* (2013.01); *A61K 36/9068* (2013.01); *A61P 11/00* (2018.01); *A61P 31/14* (2018.01); *A61K 2236/331* (2013.01)

(58) Field of Classification Search
CPC .. A61K 36/575; A61K 36/725; A61K 36/882; A61K 36/9068; A61K 2236/331; A61P 36/9068; A61P 11/00
See application file for complete search history.

(56) References Cited

FOREIGN PATENT DOCUMENTS

| | | |
|---|---|---|
| CN | 100339101 C | 9/2007 |
| CN | 101947304 A | 1/2011 |
| CN | 104523929 A | 4/2015 |
| CN | 111407877 A | 7/2020 |
| KR | 920017667 A | 10/1992 |
| KR | 20150115709 A | 10/2015 |

OTHER PUBLICATIONS

Joel Penner, Herb Formulas, 2018, American Dragon, pp. 1-7. (Year: 2018).*
International Search Report and Written Opinion dated Dec. 11, 2020, for Application No. PCT/CN2020/128753.
Summary of Chinese Medicine Prescriptions for Prevention and Treatment of New Coronavirus Pneumonia, Feb. 4, 2020, available at htt https://new.qq.com/rain/a/20200204A005UQ00, last accessed Feb. 6, 2023.

Changchun University of Chinese Medicine, "The Affiliated Hospital's 'Dehumidification and Anti-Epidemic Powder' was Approved as a Medical Institution Preparation," Feb. 6, 2020, available at https://www.sohu.com/a/371005908_693295, last accessed Feb. 6, 2023.
Wangqing County Hospital of Traditional Chinese Medicine, "Advice from TCM Experts on Herbal Tea Substitutes for the Prevention of Novel Coronavirus Pneumonia," Feb. 2, 2020, available at https://m.sohu.com/a/370129955_783122, last accessed Feb. 6, 2023.
"Should patients with new coronary pneumonia take traditional Chinese medicine as soon as possible? The academician of the Chinese Academy of Sciences said so," *Beiwan New Vision Comprehensive People's Daily Overseas Edition,* Feb. 21, 2020, available at https://baijiahao_baidu.com/s?id=1659105562646034668&wfr=spider&for=pc, last accessed Feb. 6, 2023.
Zhang, Mei, "Research on Optimum Preparation Technology for Extraction Process and Inclusion Process of Volatile Oil from PingWeiSan by Orthogonal Design," Asia-Pacific Traditional Medicine, vol. 11, No. 9 (May 2015).
Sun, Shiyou, Chinese Medical Formula; Cold Pathogenic Disease and Epidemic Febrile Disease, pp. 881-882 (Mar. 31, 2015).
Zhang, Mei, "Study on the Standardization of the Classic Prescription of Pingweisan Dispensing Granules," *Chinese Masters Theses Full-text Database,* No. 5, pp. 8-17 and 31-47 (May 15, 2017).
Office of the National Health Commission of the People's Republic of China; Office of the National Administration of Traditional Chinese Medicine, "Pneumonia Treatment Protocol for Novel Coronavirus Infection (Trial Version 4)," *National Health Commission of the People's Republic of China,* Jan. 27, 2020.
Sun, Jinshan et al., "Preparation of Common Formulations," *Refined Pharmacology,* pp. 73-74 (Jun. 30, 2018).
European Search Report, dated Sep. 21, 2023, for European Application No. 20934699.8.
European Communication pursuant to Article 94(3) EPC, dated Jun. 11, 2025, for European Application No. 20934699.8.
Korean Office Action, dated Nov. 22, 2024, for Korean Application No. 10-2022-7043043.
Korean Notice of Allowance, dated Aug. 14, 2025, for Korean Application No. 10-2022-7043043.
Japanese Decision to Grant a Patent, dated Nov. 5, 2024, for Japanese Application No. 2022-567780.
Japanese First Office Action, dated Feb. 20, 2024, for Japanese Application No. 2022-567780.
Japanese Second Office Action, dated Jun. 28, 2024, for Japanese Application No. 2022-567780.

* cited by examiner

TRADITIONAL CHINESE MEDICINE COMPOSITION FOR TREATING NOVEL CORONAVIRUS PNEUMONIA, PREPARATION METHOD, DETECTION METHOD, AND USE THEREOF

CROSS-REFERENCE TO RELATED APPLICATIONS

The present disclosure claims the priority of the Chinese patent application with the application number of CN202010384148.5 and the title of "Traditional Chinese Medicine Composition for Treating Novel Coronavirus Pneumonia, Preparation Method, Detection Method and Use Thereof" filed with the Chinese Patent Office on May 8, 2020, the contents of which are incorporated by reference herein in their entirety.

TECHNICAL FIELD

The present disclosure relates to the technical field of traditional Chinese medicine, specifically, to a traditional Chinese medicine composition for treating cold dampness diseases, and in particular to a traditional Chinese medicine composition for treating Novel coronavirus pneumonia, a preparation method, a detection method and use thereof.

BACKGROUND ART

According to the nature of the pathogen, cold epidemic disease can be classified into "seasonal cold epidemic disease" and "pestilential cold epidemic disease". Pestilential cold epidemic disease is an exogenous disease with strong epidemic infectivity caused by the feeling of yin-cold toxin. Pestilential cold epidemic disease can be divided into four categories: cold pestilence, cold-dampness pestilence, cold-dryness dampness pestilence, and yin-poison pestilence. Among them, cold-dampness pestilence is relatively common, and its clinical manifestations are: aversion to cold and fever, headache without sweat, aching limbs and joints, bitter and slightly thirsty in the mouth, thin, white and slightly greasy coated tongue, and floating or tight pulse condition, which are mainly caused by cold-evil mixed with filthy dampness. Therefore, the general treatment principle is "dispelling cold and expelling dampness, avoiding filth and removing turbidity".

Novel coronavirus is a new coronavirus strain that has never appeared in the human body before. The common signs of people infected with coronavirus include respiratory symptoms, fever, cough, shortness of breath and dyspnea, etc. In more serious cases, infection can lead to pneumonia, severe acute respiratory syndrome or renal failure, or even death. At present, there is no specific treatment method for diseases caused by novel coronavirus. Among the confirmed patients with novel coronavirus, many of them have fat and large tongue, tooth marks, thick greasy coated tongue, or even curdy fur, all of which show the characteristics of "dampness". Combined with the clinical manifestations of 2019 novel coronavirus pneumonia, this novel coronavirus pneumonia mainly presents a characteristic of "dampness", with either cold or fever. Therefore, it is necessary to provide a traditional Chinese medicine composition for treating cold dampness diseases, especially for treating Novel coronavirus pneumonia.

In view of this, the present disclosure is hereby proposed.

SUMMARY

The first object of the present disclosure is to provide a traditional Chinese medicine composition, which can treat cold dampness diseases, especially novel coronavirus pneumonia, and has remarkable curative effect.

The second object of the present disclosure is to provide a preparation method of the traditional Chinese medicine composition which can fully extract the effective ingredients of the traditional Chinese medicine composition, and has high bioavailability. The preparation method is simple without any special equipment, and thus is suitable for industrial production.

The third object of the present disclosure is to provide the use of the traditional Chinese medicine composition in preparing drugs for treating cold dampness diseases, especially novel coronavirus pneumonia.

To achieve the above objects, the technical solution adopted in the present disclosure is as follows.

Provided is an traditional Chinese medicine composition for treating novel coronavirus pneumonia, and this traditional Chinese medicine composition is mainly prepared from the following raw materials in parts by weight: 250-400 parts of *Citri reticulatae pericarpium,* 100-200 parts of *Rhizoma Atractylodis,* 100-200 parts of *Cortex Magnoliae Officinalis,* 200-300 parts of *Radix Glycyrrhizae,* 200-300 parts of *Herba Agastaches,* 200-300 parts of *Acorus tatarinowii,* 250-330 parts of *Ziziphus jujuba Mill.,* and 100-200 parts of *Zingiber officinale Roscoe.*

In one preferred embodiment, the traditional Chinese medicine composition is mainly prepared from the following raw materials in parts by weight: 270-350 parts of *Citri reticulatae pericarpium,* 130-175 parts of *Rhizoma Atractylodis,* 130-175 parts of *Cortex Magnoliae Officinalis,* 200-260 parts of *Radix Glycyrrhizae,* 200-260 parts of *Herba Agastaches,* 200-260 parts of *Acorus tatarinowii,* 280-330 parts of *Ziziphus jujuba Mill.,* and 150-180 parts of *Zingiber officinale Roscoe.*

*Citri reticulatae pericarpium* is dried and mature peel of Citrus reticulata and its cultivated varieties in Rutaceae family. It is fragrant and warm in nature, and belongs to the lung and spleen meridian. It has the effects of regulating Qi, strengthening spleen, eliminating dampness and reducing phlegm. The main ingredients of *Citri reticulatae pericarpium* mainly include flavonoid compounds, volatile oils, limonoids, alkaloids and trace elements (calcium, potassium, magnesium, sodium, lithium, iron, zinc or manganese, etc.).

In the present disclosure, the typical but non-limiting content of *Citri reticulatae pericarpium* is 250 parts by weight, 270 parts by weight, 290 parts by weight, 310 parts by weight, 330 parts by weight, 350 parts by weight, 370 parts by weight, 390 parts by weight, or 400 parts by weight.

*Rhizoma Atractylodis* is dried rhizome of the plant *Atractylis lancea* Thunb. or *Atractylis chinensis* (Bunge) DC. of Asteraceae Bercht. & J. Presl. It is pungent, bitter and/or warm in nature and belongs to the spleen, stomach and/or liver meridian. It has the effect of eliminating dampness and strengthening spleen, dispelling wind and expelling cold, and improving eyesight. Clinically, it is used for the treatment of damp blockage of spleen and stomach, abdominal distention, diarrhea, edema, beriberi, rheumatism arthralgia, common cold due to wind-cold, night blindness, and dry eyes. The experiments have proved that *Rhizoma Atractylodis* has anti-inflammatory and bacteriostatic effects. *Rhizoma Atractylodis* mainly contains volatile oil, which is composed of a series of sesquiterpene, polyethylene alkynes and a small amount of phenols and/or organic acids. In addition, it also contains sesquiterpene lactones, sesquiterpene glycosides, polysaccharides and a small amount of flavonoids, of which the main active ingredients are sesquiterpenoids and polyethylene alkynes.

In the present disclosure, the typical but non-limiting content of *Rhizoma Atractylodis* is 100 parts by weight, 110 parts by weight, 120 parts by weight, 130 parts by weight, 140 parts by weight, 150 parts by weight, 160 parts by weight, 170 parts by weight, 180 parts by weight, 190 parts by weight, or 200 parts by weight.

*Cortex Magnoliae Officinalis* is the dry bark, root bark and branch bark of plant *Cortex Magnoliae Officinalis* or *Magnolia officinalis Rehd. et Wils.* subsp. *Biloba (Rehd. et Wils.)* Cheng et Law of *Magnoliaceae Juss.* It is bitter, pungent, and warm in nature, and belongs to the spleen, stomach, lung and/or large intestine meridian. It has the effect of eliminating dampness and dissolving phlegm, descending Qi and relieving distention. Clinically, it is used for the treatment of damp heat in the spleen and the stomach, gastric distension and vomiting and diarrhoea, food accumulation and Qi stagnation, abdominal distension and constipation, dyspnea with cough caused by phlegm and retained fluid. The experiments have proved that *Cortex Magnoliae Officinalis* has anti-virus, anti-bacterial, analgesic and anti-inflammatory effects. *Cortex Magnoliae Officinalis* mainly contains lignans, alkaloids, phenylethanol glycosides, phenol glycosides and/or volatile oils.

In the present disclosure, the typical but non-limiting content of *Cortex Magnoliae Officinalis* is 100 parts by weight, 110 parts by weight, 120 parts by weight, 130 parts by weight, 140 parts by weight, 150 parts by weight, 160 parts by weight, 170 parts by weight, 180 parts by weight, 190 parts by weight, or 200 parts by weight.

*Radix Glycyrrhizae* is the dried roots and rhizomes of the plant *Radix Glycyrrhizae, Glycyrrhiza inflata Batalin* or *Glycyrrhiza glabra* L. of Leguminosae. It has sweet flavor, is neutral in nature, and belongs to the heart, lung, spleen and stomach meridian. It has the effects of tonifying spleen and Qi, clearing away heat and toxic material, expelling phlegm and arresting coughing, relieving spasm and pain, and coordinating the drug actions of a prescription. Clinically, it is used for the treatment of weakness of the spleen and the stomach, fatigue and lack of strength, palpitations and shortness of breath, cough and sputum production, abdominal distention and/or spasm and pain in the extremities, carbuncle and skin ulcer, and can relieve drug toxicity and severity. The experiments have proved that *Radix Glycyrrhizae* has effects of anti-inflammatory, anti-bacteria and/or eliminating phlegm and relieving cough. The chemical ingredients of *Radix Glycyrrhizae* mainly include triterpenoids, flavonoids and glycyrrhiza polysaccharides.

In the present disclosure, the typical but non-limiting content of *Radix Glycyrrhizae* is 200 parts by weight, 210 parts by weight, 220 parts by weight, 230 parts by weight, 240 parts by weight, 250 parts by weight, 260 parts by weight, 270 parts by weight, 280 parts by weight, 290 parts by weight, or 300 parts by weight.

*Herba Agastaches* is the dry aboveground part of the *Labiatae* plant *Pogostemon cablin.* It is pungent, slightly warm in nature, and belongs to spleen, stomach and/or lung meridian. It has the effects of eliminating dirty substance with fragrance, controlling nausea and vomiting, relieving superficies syndrome and relieving summer heat. Clinically, it is used for the treatment of damp blockage of spleen and stomach, gastric distension and vomiting, syndrome of summer-heat and damp, damp-warm syndrome in the early stage, fever and lassitude, chest oppression, cold-dampness and severe heatstroke, bellyache and vomiting and diarrhoea, and rhinorrhea and headache. The experiments have proved that it has anti-virus, anti-bacterial, analgesic and anti-inflammatory effects. The main active ingredients of *Herba Agastaches* are patchouli alcohol and patchouli ketone.

In the present disclosure, the typical but non-limiting content of *Herba Agastaches* is 200 parts by weight, 210 parts by weight, 220 parts by weight, 230 parts by weight, 240 parts by weight, 250 parts by weight, 260 parts by weight, 270 parts by weight, 280 parts by weight, 290 parts by weight, or 300 parts by weight.

*Acorus tatarinowii* is the dry rhizome of *Araceae* plant *Acorus tatarinowii.* It is pungent, bitter, and warm in nature, and belongs to heart, and stomach meridian. It has the functions of opening the orifices and sweeping phlegm, inducing resuscitation and improving intelligence, and resolving dampness and whetting the appetite. Clinically, it is used for the treatment of dizziness and epilepsy, being forgetful and insomnia, tinnitus and deafness, abdominal distension and impaired appetite, and food-denying and dysentery. The experiments have proved that *Acorus tatarinowii* contains many antispasmodic and antiasthmatic ingredients, and its decoctum can promote the secretion of digestive juice and relieve the spasm of intestinal smooth muscle. Modern pharmacological research shows that its chemical ingredients are mainly volatile ingredients and non-volatile ingredients. Currently, the study of volatile parts is more than that of non-volatile parts. The volatile ingredients are relatively complex, with more than 60 known types, in which the main structural types are compounds of phenylpropanoids (simple phenylpropanoids, lignans and coumarins) and terpenoids (monoterpenes, sesquiterpenes, diterpenes and triterpenes). Non-volatile ingredients mainly include alkaloids, aldehydes and acids, quinones and ketones, sterols, amino acids, and sugars, etc.

In the present disclosure, the typical but non-limiting content of *Acorus tatarinowii* are 200 parts by weight, 210 parts by weight, 220 parts by weight, 230 parts by weight, 240 parts by weight, 250 parts by weight, 260 parts by weight, 270 parts by weight, 280 parts by weight, 290 parts by weight, or 300 parts by weight.

*Ziziphus jujuba Mill.* is the dried and mature fruit of the plant *Ziziphus jujuba Mill.* of *Rhamnaceae* Juss. It is sweet and warm in nature, and belongs to spleen, stomach and/or heart meridian. It has the effects of tonifying middle-Jiao and Qi, nourishing the blood and tranquilization. Clinically, it is used for the treatment of insufficiency of the spleen and loss of appetite, fatigue and loose stools, and hysteria of woman. The experiments have proved that *Ziziphus jujuba Mill.* has effects of inhibiting nerves, protecting liver, enhancing muscle strength, fighting cancer, fighting mutation and fighting lipid peroxidation. The volatile oil ingredients of *Ziziphus jujuba Mill.* mainly contain dimethyl phthalate, ethyl tridecanoate, diisobutyl phthalate, 3-hydroxy-2-butanone, furfuryl alcohol, 2-cyclopentene-1,4-dione, ethyl palmitate and/or methyl linolenate, etc.

In the present disclosure, the typical but non-limiting content of *Ziziphus jujuba Mill.* is 250 parts by weight, 260 parts by weight, 270 parts by weight, 280 parts by weight, 290 parts by weight, 300 parts by weight, 310 parts by weight, 320 parts by weight, or 330 parts by weight.

*Zingiber officinale Roscoe* is the fresh rhizome of *Zingiberaceae* plants. It is pungent and slightly warm in nature, and belongs to lung, spleen and/or stomach meridian. It has the effects of relieving superficies syndrome and dissipating cold, warming the middle-Jiao to arrest vomiting, removing phlegm and stopping coughing, and resolving the toxin of fish and crabs. It is used for the treatment of common cold due to wind-cold, stomach cold and vomiting, cold phlegm and cough, and poisoning from fish and crabs. The experiments have proved that *Zingiber officinale Roscoe* has effects of inhibiting nerves, protecting liver, enhancing muscle strength, fighting cancer, fighting mutation and fighting lipid peroxidation. Modern research shows that the main ingredients of *Zingiber officinale Roscoe* are volatile oils, gingerols and diphenyl heptanes.

In the present disclosure, the typical but non-limiting content of *Zingiber officinale Roscoe* is 100 parts by weight, 110 parts by weight, 120 parts by weight, 130 parts by weight, 140 parts by weight, 150 parts by weight, 160 parts by weight, 170 parts by weight, 180 parts by weight, 190 parts by weight, or 200 parts by weight.

In one preferred embodiment, the traditional Chinese medicine composition of the present disclosure consists of following raw materials in parts by weight: 340.9 parts of *Citri reticulatae pericarpium*, 170.5 parts of *Rhizoma Atractylodis*, 170.5 parts of *Cortex Magnoliae Officinalis*, 255.7 parts of *Radix Glycyrrhizae*, 255.7 parts of *Herba Agastaches*, 255.7 parts of *Acorus tatarinowii*, 318.2 parts of *Ziziphus jujuba Mill.*, and 163.6 parts of *Zingiber officinale Roscoe.*

In one embodiment, the traditional Chinese medicine composition of the present disclosure also contains a certain parts by weight of adjuvant material, preferably 500-700 parts by weight of adjuvant material; preferably, the adjuvant material is filler.

More preferably, the filler is dextrin, soluble starch or lactose.

The traditional Chinese medicine composition of the present disclosure can be prepared into various preparations through conventional techniques in the art, including but not limited to oral liquid, granule, pulvis, dropping pill, capsule, effervescing agent or tablet, etc.

In one embodiment, the method for preparing the traditional Chinese medicine composition of the present disclosure includes the following steps:

soaking the raw materials in parts by weight with water, decocting and extracting, filtering to obtain an extracted solution, concentrating the extracted solution under reduced pressure, drying by spray, so as to obtain the spray-dried powder; mixing the powder with adhesive and granulating by wet method.

In one specific embodiment, the method for preparing the traditional Chinese medicine composition of the present disclosure includes the following steps:

(1) weighing each raw material component according to parts by weight;

(2) adding 15 times parts by weight of water, soaking for 0.5 h, decocting and extracting twice with 0.5 h each time, combining the decoction and filtering to obtain an extracted solution for future use;

(3) concentrating the extracted solution in step (2) at 70° C. under reduced pressure to the concentrate with relative density of 1.10-1.20 g/mL measured at 50° C.;

(4) taking the concentrate in step (3) and drying it by spray to obtain a spray-dried powder;

(5) mixing the spray-dried powder in step (4) with dextrin and granulating by wet method.

In one preferred embodiment, the spray drying condition of the above step (4) is: inlet temperature of 125° C., pressure of 102.5 MPa, blow of 80%, and flow rate of 20-30/s.

In another embodiment, the method for preparing the traditional Chinese medicine composition of the present disclosure includes the following steps:

extracting the raw materials in parts by weight by steam distillation method, and collecting the volatile oil at the same time;

filtering off the residue from the decoction to obtain an extracted solution;

concentrating the extracted solution under reduced pressure and drying by spray to obtain the spray-dried powder;

adding anhydrous ethanol solution into the volatile oil, and preparing a cyclodextrin inclusion complex by inclusion of cyclodextrin aqueous solution;

mixing the spray-dried powder and the volatile oil inclusion complex with adhesive and granulating by wet method.

In one preferred embodiment, in the method for preparing the traditional Chinese medicine composition of the present disclosure, the steam distillation method is performed for 2-3 times, and the extracted solutions obtained each time are combined for the next step.

In one preferred embodiment, in the method for preparing the traditional Chinese medicine composition of the present disclosure, 8-15 times the amount of water is added to extract the volatile oil in the steam distillation method.

In one preferred embodiment, in the β-cyclodextrin aqueous solution, the weight of β-cyclodextrin is 8-12 times that of the volatile oil, and the weight of water is 10-20 times that of β-cyclodextrin; preferably, the weight of β-cyclodextrin is 10 times that of the volatile oil, and the weight of water is 15 times that of β-cyclodextrin.

In another specific embodiment, the method for preparing the traditional Chinese medicine composition of the present disclosure includes the following steps:

(a) weighing each raw material ingredient in part by weight and crushing them into coarse powder;

(b) adding 8-15 times parts of weight of water, soaking for 0.5 h, then extracting by steam distillation method, and collecting the volatile oil at the same time; filtering off the residue from the decoction to obtain an extracted solution for future use;

(c) concentrating the extracted solution obtained in step (b) under reduced pressure to the concentrate with relative density of 1.10-1.20 g/mL measured at 60° C.;

(d) taking the concentrate in step (c) and drying it by spray to obtain a spray-dried powder;

(e) adding absolute ethanol solution to the volatile oil collected in step (b), and then stirring with β-cyclodextrin aqueous solution for 3 h for inclusion, refrigerating and filtering the resultant, drying the filtered product to obtain volatile oil inclusion complex;

(f) mixing the spray-dried powder in step (d) and the volatile oil inclusion complex in step (e) with dextrin and granulating by wet method.

In one preferred embodiment, in step (b), the residue is added with 8-15 times amount of water to continue to be extracted by steam distillation method for 1 h, and the extracted solution is obtained after the decoction is filtered; the extracted solutions obtained twice are combined for the next step.

In one preferred embodiment, in step (b), concentration under reduced pressure is carried out at 70° C.; in step (c), the condition for spray drying is: inlet temperature of 160-180° C., and outlet temperature of 80-90° C.

In one preferred embodiment, in step (e), in the β-cyclodextrin aqueous solution, the weight of β-cyclodextrin is 8-12 times that of the volatile oil, and the weight of water is 10-20 times that of β-cyclodextrin; preferably, the weight of β-cyclodextrin is 10 times that of the volatile oil, and the weight of water is 15 times that of β-cyclodextrin.

In one embodiment, the present disclosure provides a quality detection method of the traditional Chinese medicine composition, including qualitative identification of hesperidin by thin-layer chromatography and content determination of hesperidin, preferably, further including qualitative identification of 6-gingerol, *Radix Glycyrrhizae* and magnolol by thin-layer chromatography.

In one specific embodiment, qualitative identification by thin-layer chromatography includes:

(1) dissolving 2 g of the granular powder made of the traditional Chinese medicine composition in 25 mL of water, shaking and extracting the obtained solution twice using ethyl acetate with 20 mL each time, combining the extracted solution and evaporating to dryness, dissolving the residue by adding 1 mL of methanol, which is used as the test solution; adding methanol into hesperidin reference sample to prepare saturated solution as the reference solution; according to thin-layer chromatography, sampling 2-5 μL of the test solution and 5 μL of the reference solution, dotting these two solutions on the same silica gel G thin layer plate respectively, spreading by using as the developing solvent ethyl acetate-methanol-water with a volume ratio of 20:3: 2, taking out the plate and drying, spraying 5% aluminum trichloride-ethanol solution, heating at 105° C. for 5-10 min, and placing under the ultraviolet lamp at 365 nm for inspection, wherein in the chromatogram of the test sample, spots of the same color are shown at the corresponding position of the chromatogram of the reference medicine;

(2) using the test solution in (1) as the test sample, adding ethyl acetate into 6-gingerol reference sample to prepare a solution containing 1 mg per 1 mL as the reference solution; according to thin-layer chromatography, sampling 3-10 μL of the test solution and 1 μL of the reference solution, dotting these two solutions on the same silica gel G thin layer plate respectively; spreading by using as the developing solvent petroleum ether (60-90° C.) -trichloromethane-ethyl acetate with a volume ratio of 2:1:1, taking out the plate and drying, spraying 2% vanillin-sulfuric acid solution, heating at 105° C. until the spot shows a clear color, wherein in the chromatogram of the test sample, spots of the same color are shown at the corresponding position of the chromatogram of the reference sample;

(3) dissolving 3 g of granules made of the traditional Chinese medicine composition by adding 40 mL of water, shaking and extracting the obtained solution three times using n-butanol with 20 mL each time, combining the n-butanol solution with 20 mL each time and evaporating to dry the n-butanol solution, dissolving the residue by adding 1 mL of methanol, which is used as the test solution; refluxing 1 g of *Radix Glycyrrhizae* reference drug by adding 40 mL of water for 1 h, cooling and filtering, shaking and extracting the obtained solution three times using n-butanol with 20 mL each time, combining the n-butanol solution with 20 mL each time and evaporating to dry the n-butanol solution, dissolving the residue by adding 1 mL of methanol, which is used as the reference solution; according to thin-layer chromatography, sampling 2-5 μL of the test solution and 5 μL of reference medicine solution, dotting these two solutions on a silica gel G thin layer plate respectively, spreading by using as the developing solvent ethyl acetate-formic acid-glacial acetic acid-water with a volume ratio of 15:1:1:2, taking out the plate and drying, spraying 10% sulfuric acid-ethanol solution, heating at 105° C. until the spot shows a clear color, and placing under the ultraviolet lamp at 365 nm for inspection, wherein in the chromatogram of the test sample, fluorescent main spots of the same color are shown at the corresponding position of the chromatogram of the reference medicine;

(4) grinding 6 g of granules made of the traditional Chinese medicine composition, adding 40 mL of ethyl acetate, performing ultrasonic treatment for 30 minutes, filtering the obtained solution, evaporating the filtrate to dryness, dissolving the residue by adding 1 mL of methanol, which is used as the test solution; adding methanol into magnolol to prepare a mixed solution containing 1 mg per 1 mL as a reference solution; according to thin-layer chromatography, sampling 10-15 μL of the test solution and 5 μL of the reference solution, dotting these two solutions on the same silica gel G thin layer plate respectively; spreading by using as the developing solvent toluene-ethyl acetate-methanol with a volume ratio of 18:3:1, taking out the plate and drying, spraying 1% vanillin-sulfuric acid solution, heating at 105° C. until the spot shows a clear color, wherein in the chromatogram of the test sample, spots of the same color are shown at the corresponding position of the chromatogram of the reference sample.

In one specific embodiment, the content of hesperidin is determined by high performance liquid chromatography as follows:

octadecylsilane bonded silica gel is used as filler; acetonitrile: 0.1% phosphoric acid solution=19:81 by volume is as mobile phase;

the detection wavelength is 283 nm, and the flow rate is 1.0 mL/min;

the number of theoretical plates is not less than 2000 according to the hesperidin peak;

preparation of reference solution: an appropriate amount of hesperidin reference sample is accurately weighed, and added with methanol to prepare a solution which contains 15 μg per 1 mL, which is the reference solution;

preparation of test solution: the traditional Chinese medicine composition of the present disclosure is finely ground, and sieved through No. 5 sieve, and 0.3 g of the resultant is precisely weighed and placed in a conical flask with a stopper; 50 mL of 10% methanol is accurately added into the flask, and weighted, followed by ultrasonic treatment for 30 minutes, cooling, weighing again, supplementing the lost weight with methanol, shaking the solution, filtering, and collecting the subsequent filtrate, which is the test solution;

determination method: 10 μl of the reference solution and 10 μl of the test solution are accurately sampled respectively, and injected in the liquid chromatograph for measurement; and each 1 g of the particles of this composition contains no less than 2.325 mg of *Citri reticulatae pericarpium* in terms of hesperidin ($C_{28}H_{34}O_{15}$).

By measuring the content of hesperidin in granules of the traditional Chinese medicine composition, the present disclosure can ensure the stability and controllability of the quality of granules on one hand, and on the other hand can ensure the content of the effective ingredients of the traditional Chinese medicine composition through the determination of hesperidin content and transfer rate due to the stable physical and chemical properties of hesperidin so as to effectively control the product quality better.

Use of the above traditional Chinese medicine composition in preparation of drugs for treating cold dampness diseases; optionally, use of the traditional Chinese medicine composition in preparation of drugs for treating novel coronavirus pneumonia.

The beneficial effects of the present disclosure are as follows.

The traditional Chinese medicine preparation provided by the present disclosure is composed of *Citri reticulatae pericarpium, Rhizoma Atractylodis, Cortex Magnoliae Officinalis, Radix Glycyrrhizae, Herba Agastaches, Acorus tatarinowii, Ziziphus jujuba Mill.*, and *Zingiber officinale Roscoe* in a certain parts by weight, and active ingredients in these herbs complement each other. Through the compatibility relationship of the individual raw material herbs, the traditional Chinese medicine preparation obtained has little side effects, can treat cold dampness diseases, especially novel coronavirus pneumonia, achieving significant therapeutic effect.

The preparation method of the present disclosure can fully extract the effective ingredients of the traditional Chinese medicine composition, and has high bioavailability. The preparation method is simple without any special equipment, and thus is suitable for industrial production. The preparation method of the present disclosure improves hesperidin in the traditional Chinese medicine composition on its content and its transfer rate.

The detection method of the present disclosure can effectively control the quality of the traditional Chinese medicine composition, thereby making it have good stability and reproducibility.

Since the traditional Chinese medicine ingredients in the present disclosure mostly contain volatile oil ingredients, the comprehensive method of steam distillation extraction and volatile oil inclusion reduces the loss of volatile oil, shortens the process time, improves the utilization rate of volatile oil in the finished product of the traditional Chinese medicine preparation, and makes the medicinal effect of the traditional Chinese medicine composition better.

BRIEF DESCRIPTION OF DRAWINGS

The embodiments of the present disclosure are described in detail below in combination with the accompanying drawings, wherein.

Figure 1:
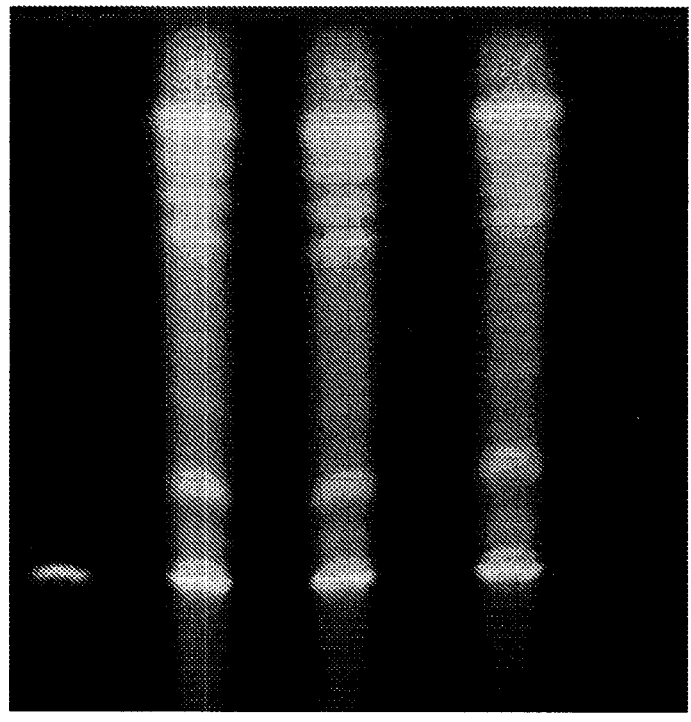
FIG. 1 is the chromatogram of qualitative identification by the thin-layer chromatography of hesperidin in Example 6 of the present disclosure, in which one column on the left is for the reference solution, and three columns on the right are for the test solutions of the traditional Chinese medicine granules of the present disclosure.
Figure 2:
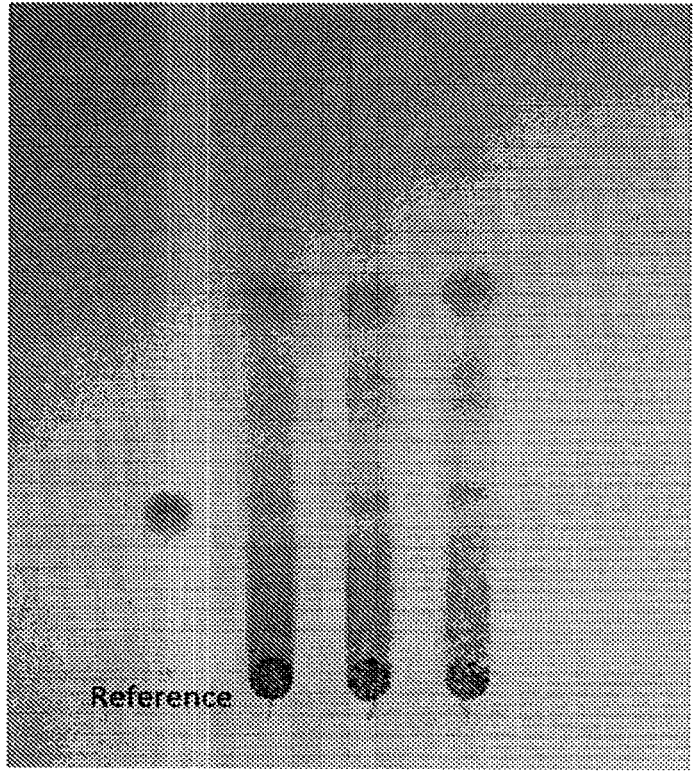
FIG. 2 is the chromatogram of qualitative identification by the thin-layer chromatography of 6-gingerolin in Example 6 of the present disclosure, in which one column on the left is for the reference solution, and three columns on the right are for the test solutions of the traditional Chinese medicine granules of the present disclosure.
Figure 3:
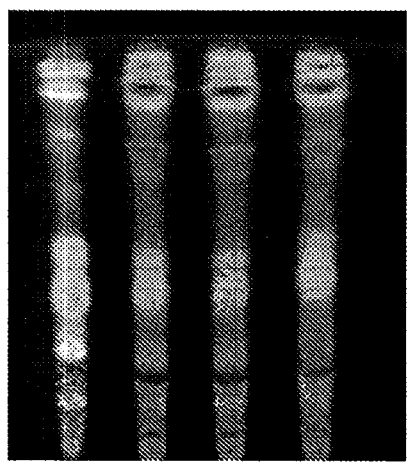
FIG. 3 is the chromatogram of qualitative identification by the thin-layer chromatography of *Radix Glycyrrhizae* in Example 6 of the present disclosure, in which one column on the left is for the reference solution, and three columns on the right are for the test solutions of the traditional Chinese medicine granules of the present disclosure.
Figure 4:
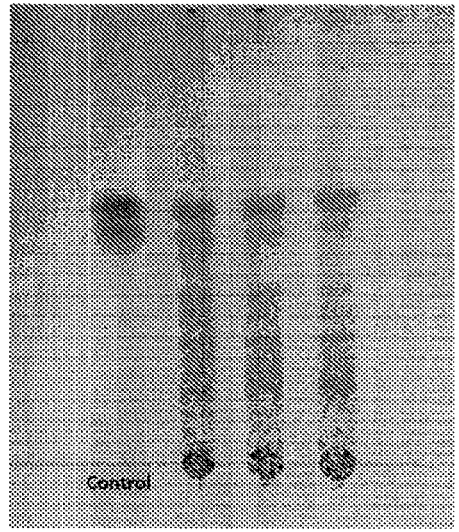
FIG. 4 is the chromatogram of qualitative identification by the thin-layer chromatography of magnolol in Example 6 of the present disclosure, in which one column on the left is for the reference solution, and three columns on the right are for the test solutions of the traditional Chinese medicine granules of the present disclosure.
Figure 5:
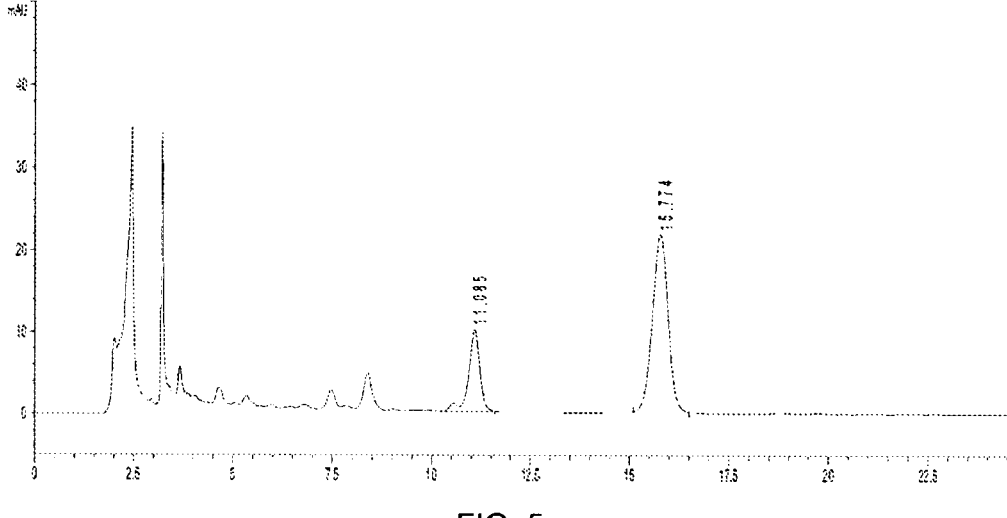
Figure 6:
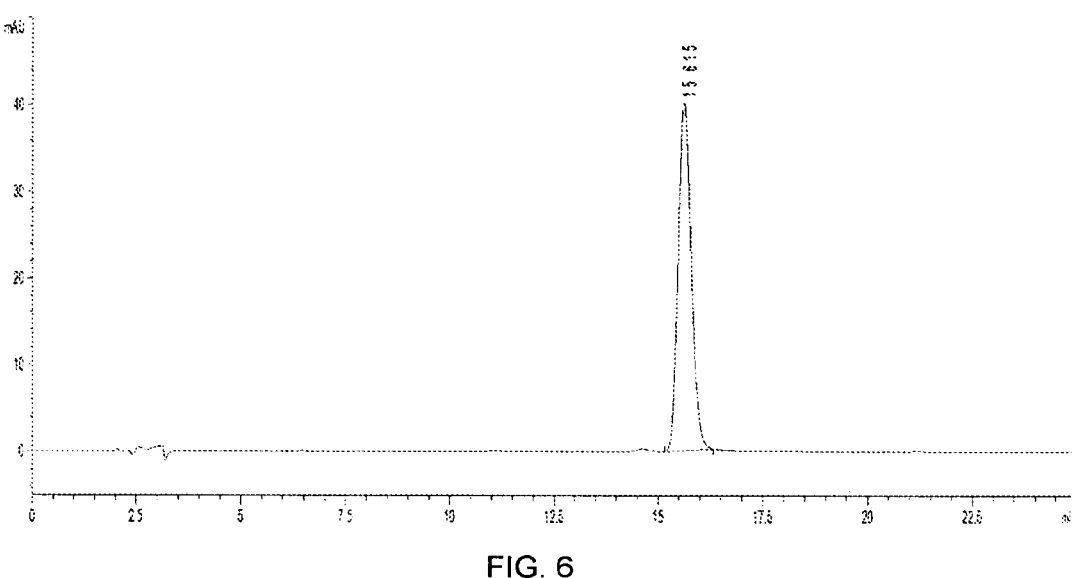
Figure 7:
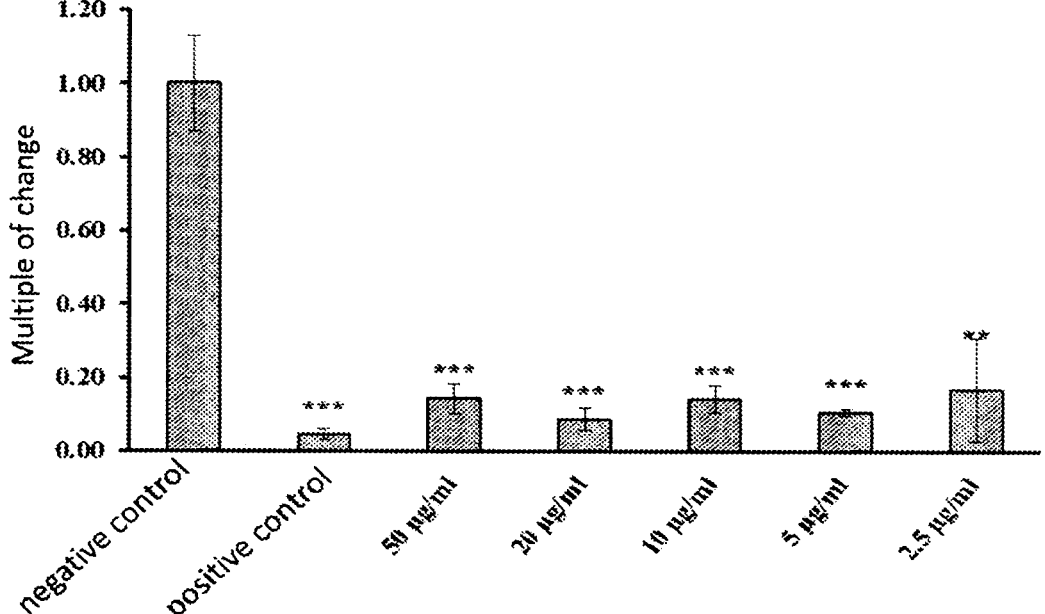

FIG. 5 is the chromatogram of high performance liquid chromatography of the test sample of Chinese traditional medicine granules of the present disclosure in the determination of hesperidin content in Example 7 of the present disclosure;

FIG. 6 is the chromatogram of high performance liquid chromatography of the reference sample in the determination of hesperidin content in Example 7 of the present disclosure; and FIG. 7 shows the inhibitory effect of the Chinese traditional medicine extract of the present disclosure on HEK293-ACE2 cells infected by COVID-19 pseudovirus, in Student's t-test, compared with the negative control group, * * *P<0.001; **P<0.01.

DETAILED DESCRIPTION OF EMBODIMENTS

The embodiments of the present disclosure will be described in detail below in combination with the Examples, but those skilled in the art will understand that the following Examples are only used to explain this disclosure, and should not be considered as limiting the scope of this disclosure. If the specific conditions are not indicated in the Examples, the general conditions or the conditions recommended by the manufacturer shall be followed. The reagents or instruments used without manufacturer's name are conventional products that can be purchased from the market.

The traditional Chinese medicine composition of the present disclosure will be further described in detail below in combination with Examples 1-7 and Comparative Examples 1-3.

Example 1

To prepare the traditional Chinese medicine composition in this disclosure, the raw materials were weighed according to the following parts by weight: 7.5 g of *Citri reticulatae pericarpium*, 3.75 g of *Rhizoma Atractylodis*, 3.75 g of *Cortex Magnoliae Officinalis*, 5.625 g of *Radix Glycyrrhizae*, 5.625 g of *Herba Agastaches*, 5.625 g of *Acorus tatarinowii*, 3.5 g of *Ziziphus jujuba Mill.*, and 1.8 g of *Zingiber officinale Roscoe*. The resultant was added with proper amount of water, and decocted with gentle heat to 400 mL to make decoction.

Example 2

To prepare the traditional Chinese medicine composition in this disclosure, the raw materials were weighed according to the following parts by weight: 250 g of *Citri reticulatae pericarpium*, 100 g of *Rhizoma Atractylodis*, 100 g of *Cortex Magnoliae Officinalis*, 200 g of *Radix Glycyrrhizae*, 200 g of *Herba Agastaches*, 200 g of *Acorus tatarinowii*, 250 g of *Ziziphus jujuba Mill.*, and 100 g of *Zingiber officinale Roscoe*. The resultant was added with 15 times parts by weight of water, soaked for 0.5 h, then decocted and extracted twice with 0.5 h each time, and the detection was combined and filtered to obtain the extracted solution for future use. The extracted solution was concentrated at 70° C. under reduced pressure to a concentrate with relative density of 1.10-1.20 g/mL measured at 50° C. The concentrate was dried by spray to obtain the spray-dried powder, which was added with proper amount of dextrin for mixing, and granulating by wet method was carried out.

Example 3

To prepare the traditional Chinese medicine composition in this disclosure, the raw materials were weighed according to the following parts by weight: 400 g of *Citri reticulatae pericarpium*, 200 g of *Rhizoma Atractylodis*, 200 g of *Cortex Magnoliae Officinalis*, 300 g of *Radix Glycyrrhizae*, 300 g of *Herba Agastaches*, 300 g of *Acorus tatarinowii*, 330 g of *Ziziphus jujuba Mill.*, and 200 g of *Zingiber officinale Roscoe*. The resultant was added with 15 times parts by weight of water, soaked for 0.5 h, then decocted and extracted twice with 0.5 h each time, and the detection was combined and filtered to obtain the extracted solution for future use. The extracted solution was concentrated at 70° C. under reduced pressure to a concentrate with relative density of 1.10-1.20 g/mL measured at 50° C. The concentrate was dried by spray to obtain the spray-dried powder, which was added with dextrin for mixing, and granulating by wet method was carried out.

Example 4

To prepare the traditional Chinese medicine composition in this disclosure, the raw materials were weighed according to the following parts by weight: 375 g of *Citri reticulatae pericarpium*, 187.5 g of *Rhizoma Atractylodis*, 187.5 g of *Cortex Magnoliae Officinalis*, 281.3 g of *Radix Glycyrrhizae*, 281.3 g of *Herba Agastaches*, 281.3 g of *Acorus tatarinowii*, 330 g of *Ziziphus jujuba Mill.*, and 180 g of *Zingiber officinale Roscoe*. The resultant was added with 15 times parts by weight of water, then soaked for 0.5 h, decocted and extracted twice with 0.5 h each time, and the detection was combined and filtered to obtain the extracted solution for future use. The extracted solution was concentrated at 70° C. under reduced pressure to a concentrate with relative density of 1.10-1.20 g/mL measured at 50° C. The concentrate was dried by spray to obtain the spray-dried powder, which was mixed with dextrin, and granulating by wet method was carried out.

Example 5

To prepare the traditional Chinese medicine composition in this disclosure, the raw materials were weighed according to the following parts by weight: 340.9 g of *Citri reticulatae pericarpium*, 170.5 g of *Rhizoma Atractylodis*, 170.5 g of *Cortex Magnoliae Officinalis*, 255.7 g of *Radix Glycyrrhizae*, 255.7 g of *Herba Agastaches*, 255.7 g of *Acorus tatarinowii*, 318.2 g of *Ziziphus jujuba Mill.*, and 163.6 g of *Zingiber officinale Roscoe*. The resultant was crushed into coarse powder, added with 15 times parts by weight of water, soaked for 0.5 h, then extracted by steam distillation method for 4 h while collecting the volatile oil; the decoction was filtered to remove the residue to obtain an extracted solution for future use, and residue was added with 15 times weight of water and extracted by steam distillation method for 1 h to obtain the treated decoction for future use; and the extracted solutions were combined and filtered, and the obtained extracted solution was concentrated under reduced pressure to a concentrate with relative density of 1.10-1.20 g/mL measured at 60° C. The concentrate was dried by spray to obtain the spray-dried powder. The volatile oil collected was added with absolute ethanol solution, and the resultant was stirred with β-cyclodextrin aqueous solution for 3 h for inclusion, refrigerated and filtered to obtain a filtrated product, which was dried to obtain volatile oil inclusion complex. The spray-dried powder and the volatile oil inclusion complex were mixed with dextrin, and then granulating by wet method was carried out.

Example 6

The granules of the traditional Chinese medicine composition prepared in Example 4 were identified by thin-layer chromatography as follows:

(1) dissolving 2 g of the granular powder made of the traditional Chinese medicine composition in 25 mL of water, shaking and extracting the obtained solution twice using ethyl acetate with 20 mL each time, combining the extracted solution and evaporating to dryness, dissolving the residue by adding 1 mL of methanol, which is used as the test solution; adding methanol into hesperidin reference sample to prepare saturated solution as the reference solution; according to thin-layer chromatography, sampling 2-5 μL of the test solution and 5 μL of the reference solution, dotting these two solutions on the same silica gel G thin layer plate respectively, spreading by using as the developing solvent ethyl acetate-methanol-water with a volume ratio of 20:3:2, taking out the plate and drying, spraying 5% aluminum trichloride-ethanol solution, heating at 105° C. for 5-10 min, and placing under the ultraviolet lamp at 365 nm for inspection, wherein in a chromatogram of the test sample, spots of the same color were shown at a corresponding position of a chromatogram of a reference medicine;

(2) using the test solution in (1) as the test sample, adding ethyl acetate into 6-gingerol reference sample to prepare a solution containing 1 mg per 1 mL as the reference solution; according to thin-layer chromatography, sampling 3-10 μL of the test solution and 1 μL of the reference solution, dotting these two solutions on the same silica gel G thin layer plate respectively; spreading by using as the developing solvent petroleum ether (60-90° C.) -trichloromethane-ethyl acetate with a volume ratio of 2:1:1, taking out the plate and drying, spraying 2% vanillin-sulfuric acid solution, heating at 105° C. until the spot shows a clear color, wherein in the chromatogram of the test sample, spots of the same color are shown at the corresponding position of the chromatogram of the reference sample;

(3) dissolving 3 g of granules made of the traditional Chinese medicine composition by adding 40 mL of water, shaking and extracting the obtained solution three times using n-butanol with 20 mL each time, combining the n-butanol solution with 20 mL each time and evaporating to dry the n-butanol solution, dissolving the residue by adding 1 mL of methanol, which is used as the test solution; refluxing 1 g of *Radix Glycyrrhizae* reference drug by adding 40 mL of water for 1 h, cooling and filtering, shaking and extracting the obtained solution three times using n-butanol with 20 mL each time, combining the n-butanol solution with 20 mL each time and evaporating to dry the n-butanol solution, dissolving the residue by adding 1 mL of methanol, which is used as the reference solution; according to thin-layer chromatography, sampling 2-5 μL of the test solution and 5 μL of reference medicine solution, dotting these two solutions on silica gel G thin layer plate respectively, spreading by using as the developing solvent ethyl acetate-formic acid-glacial acetic acid-water with a volume ratio of 15:1:1:2, taking out the plate and drying, spraying 10% sulfuric acid-ethanol solution, heating at 105° C. until the spot shows a clear color, and placing under the ultraviolet lamp at 365 nm for inspection, wherein in the chromatogram of the test sample, fluorescent main spots of the same color are shown at the corresponding position of the chromatogram of the reference medicine; and (4) grinding 6 g of granules made of the traditional Chinese medicine composition, adding 40 mL of ethyl acetate, performing ultrasonic treatment for 30 minutes, filtering the obtained solution, evaporating the filtrate to dryness, dissolving the residue by adding 1 mL of methanol, which is used as the test solution; adding methanol into magnolol to prepare a mixed solution containing 1 mg per 1 mL as a reference solution; according to thin-layer chromatography, sampling 10-15 µL of the test solution and 5 µL of the reference solution, dotting these two solutions on the same silica gel G thin layer plate respectively; spreading by using as the developing solvent toluene-ethyl acetate-methanol with a volume ratio of 18:3:1, taking out the plate and drying, spraying 1% vanillin-sulfuric acid solution, heating at 105° C. until the spot shows a clear color, wherein in the chromatogram of the test sample, spots of the same color are shown at the corresponding position of the chromatogram of the reference sample.

See FIG. 1-FIG. 4 for thin-layer chromatograms of the test sample and the reference sample.

Example 7

The content of granules of the traditional Chinese medicine composition prepared in Example 4 was determined by high performance liquid chromatography as follows.

Chromatographic condition and system applicability test: the octadecylsilane bonded silica gel was used as filler; acetonitrile-0.1% phosphoric acid solution (19:81) was as mobile phase; the detection wavelength was 283 nm. The number of theoretical plates should not be less than 2000 according to the hesperidin peak.

Preparation of reference solution: the hesperidin reference sample was accurately weighed, and added with methanol to prepare a solution which contained 50 µg per 1 mL, which was the reference solution.

Preparation of test solution: the granules prepared in Example 4 were well mixed and finely ground, and about 0.3 g of the resultant was precisely weighed and placed in a conical flask with a stopper; 50 mL of methanol was accurately added into the flask. The flask was sealed and weighed followed by ultrasonic treatment (with a power of 500 W and a frequency of 40 kHz) for 30 minutes, cooled, and weighed again; and methanol was added into for supplementing the lost weight, and the resultant was shaken, filtered to obtain the subsequent filtrate, which was the test solution.

Determination method: 10 µl of the reference solution and 10 µl of the test solution were accurately sampled respectively, and injected in the liquid chromatograph for measurement.

In the determination of hesperidin content, FIG. 5 shows chromatogram of high performance liquid chromatography of the test sample of traditional Chinese medicine granules of the present disclosure; and FIG. 6 shows the high performance liquid chromatogram of the reference sample.

Comparative Example 1

To prepare the traditional Chinese medicine composition, the raw materials were weighed according to the following parts by weight: 375 g of Citri reticulatae pericarpium, 187.5 g of Rhizoma Atractylodis, 187.5 g of Cortex Magnoliae Officinalis, 281.3 g of Radix Glycyrrhizae, 281.3 g of Herba Agastaches, and 281.3 g of Acorus tatarinowii. The resultant was added with 15 times parts by weight of water, soaked for 0.5 h, then decocted and extracted twice with 0.5 h each time, and the detection was combined and filtered to obtain the extracted solution for future use. The extracted solution was concentrated at 70° C. under reduced pressure to a concentrate with relative density of 1.10-1.20 g/mL measured at 50° C. The concentrate was dried by spray to obtain the spray-dried powder, which was mixed with dextrin, and granulating by wet method was carried out.

Comparative Example 2

The content of granules of the traditional Chinese medicine composition prepared in Comparative Example 1 was determined by high performance liquid chromatography as follows.

Chromatographic condition and system applicability test: octadecylsilane bonded silica gel was used as filler; acetonitrile-0.1% phosphoric acid solution (19:81) was as mobile phase; and the detection wavelength was 283 nm. The number of theoretical plates should not be less than 2000 according to the hesperidin peak.

Preparation of reference solution: hesperidin reference sample was accurately weighed, and added with methanol to prepare a solution which contained 50 µg per 1 mL, which was the reference solution.

Preparation of test solution: the granules prepared in Comparative Example 1 were well mixed and finely ground, and about 0.3 g of the resultant was precisely weighed and placed in a conical flask with a stopper; 50 mL of methanol was accurately added into the flask, The flask was sealed and weighed followed by ultrasonic treatment (with a power of 500 W and a frequency of 40 kHz) for 30 minutes, cooled, and weighed again; and methanol was added into for supplementing the lost weight, and the resultant was shaken, filtered to obtain the subsequent filtrate, which was the test solution.

Determination method: 10 µl of the reference solution and 10 µl of the test solution were accurately sampled respectively, and injected in the liquid chromatograph for measurement.

Comparative Example 3

The raw materials were weighed according to the following parts by weight: 7.5 g of Citri reticulatae pericarpium, 3.75 g of Rhizoma Atractylodis, 3.75 g of Cortex Magnoliae Officinalis, 5.625 g of Radix Glycyrrhizae, 5.625 g of Herba Agastaches, 5.625 g of Acorus tatarinowii, one jujube and three slices of ginger. The jujube and the ginger were decocted separately from the first 6 traditional Chinese medicines to make decoction.

Experimental Results of Determination for Hesperidin Content and Transfer Rate:

| | Measured actual content of hesperidin in raw material medicines (mg/g) | Transfer rate of hesperidin (%) |
|---|---|---|
| Example 7 | 46.95 | 48.77% |
| Comparative Example 2 | 46.95 | 40.34% |

The test results show that the effective ingredient hesperidin in Example 7 was significantly higher than Comparative Example 2 in terms of content and transfer rate. The reason may be that the jujube and the ginger would increase the stability of hesperidin in water.

Administration Toxicity Test

The contents and procedures related to animal testing involved in this test comply with the relevant laws and regulations on the use and management of experimental animals and the relevant provisions of the Institutional Animal Care and Use Committee (IACUC).

Materials and methods: in this test, 40 healthy SD rats were randomly divided into 4 groups, namely, solvent control group, low, medium and high dosage groups of the traditional Chinese medicine composition in the present disclosure, with 10 animals in each group, including half male and half female. The rats in each group were administrated by oral gavage of the solvent control (pure water) or the traditional Chinese medicine composition of different concentrations in the present disclosure three times, each time at an interval more than 4 h according to the administration volume of 20 mL/kg each time, wherein the administration dosages of the low, middle and high dosage groups of the traditional Chinese medicine composition in the present disclosure were 3, 9 and 37.5 g of extract/kg, respectively. The observation lasted for 14 days after administration, and the day of the first administration was defined as the first day of the test. During the test, the general condition of SD rats in each group were observed every day, the body weight was measured on the 1st, 4th, 8th and 14th days of the test, the food intake was measured on the 2nd, 5th, 8th and 12th days of the test, and on the 15th day of the test, the rats in each group were euthanized and observed by gross anatomy as planned.

Results: (1) general condition: on the first day of the test, both male and female rats in the high-dosage group had soft stools, and the urine color was abnormal and light green; the above symptoms disappeared from the second day of the test, and there was no obvious abnormality in the general performance, behavioral activity, respiratory status, facial features, body surface, feces, urine and genitalia of rats in each group, and no animal death was found during the test; (2) weight and food intake: during the test, there was no significant abnormal change in weight and food intake of rats in each group; and (3) gross anatomy observation: on the 15th day of the test, the gross anatomy observation was performed and there was no obvious abnormal change in color, shape, size and texture of the main organs or tissues such as heart, liver, spleen, lung, kidney and thymus of rats in each group.

Conclusion: under the conditions of this test, SD rats were administrated orally with 3, 9 and 37.5 g of extract/kg of the traditional Chinese medicine composition of this disclosure each time, and the maximum tolerance dose (MTD) was 37.5 g of extract/kg, which is equivalent to 168.5 g of crude drug/kg.

Clinical Test

The clinical test was carried out by using the traditional Chinese medicine composition prepared in Example 1.

(1) Object of study: patients with novel coronavirus pneumonia (wherein nucleic acid test is positive) in Danjiangkou Hospital of Traditional Chinese Medicine, and aged 13-54 years. These patients showed fever (body temperature>38° C.) and cough at the same time, total number of white blood cells and lymphocyte numbers detected by blood routine were reduced, and different degrees of ground glass shadow were shown in the lung.

(2) Treatment: administration was carried out twice a day, once in the morning and once in the evening, at 200 mL each time, for 3 days.

(3) The cure or relieve standards were as follows.

1. The white blood cell and lymphocyte counts were recovered to normal.
2. The ground glass shadow of the patient's lung was absorbed and dissipated.
3. The novel coronavirus nucleic acid result was turned to be negative when detected by using real time fluorescent RT-PCR.
4. There were no other organic diseases.

Typical Clinical Cases

1, Guo x, basic data of the patient: a 29-year-old female with a work history in the epidemic area. Symptoms include fever, cough, expectoration, lack of strength and poor appetite. Imaging examination: infection of left inferior pulmonary lobe, middle lobe of right lung, lingual segment of upper lobe of left lung and inferior lobe of right lung. Etiological examination: positive result of novel coronavirus nucleic acid test. After being treated with the traditional Chinese medicine of the present disclosure, the patient had no fever, mitigated cough and expectoration, and improved strength and appetite; pulmonary inflammation was absorbed; negative result was obtained for novel coronavirus nucleic acid test, and no other adverse reactions were found during the period.

2. Shen xx, basic data of the patient: 25-year-old male. Symptoms include fever, body ache, poor appetite and lack of strength. Imaging examination: infection of inferior lobe of right lung. Etiological examination: positive result of novel coronavirus nucleic acid test. After being treated with the traditional Chinese medicine of the present disclosure, the patient had no fever, no body ache, and improved strength and appetite; pulmonary inflammation was absorbed; negative result was obtained for novel coronavirus nucleic acid test, and no other adverse reactions were found during the period.

In Vitro Efficacy Test of the Traditional Chinese Medicine Composition of the Present Disclosure:

A study was carried out on the inhibitory effect of the traditional Chinese medicine extracts of this disclosure on HEK293 which is a cell line stably expressing ACE2 receptor, infected by COVID-19 pseudovirus.

1. Test Sample and Preparation of Administration Preparation:

Test sample: 16 g of yellowish brown powder which is the extract of the traditional Chinese medicine composition of the present disclosure (extract of Example 4); hesperidin content: 13.12 mg/g; and source: Beijing Handian Pharmaceutical Co., Ltd.

Preparation of administration preparation: 20 mg of the traditional Chinese medicine extract powder was weighed, added with 1 mL of DMSO, and mixed evenly to obtain 20 mg/mL mother liquor.

100 µL of mother liquor was added with 3900 µL of DMEM medium to prepare a concentration of 5 mg/mL. 400 µL 0.5 mg/mL solution was added with 600 µL of DMEM medium to prepare a solution with concentration of 0.2 mg/mL. 500 µL 0.2 mg/mL solution was added with 500 µL of DMEM medium to prepare a solution with concentration of 0.1 mg/mL. 500 µL 0.1 mg/mL solution was added with 500 µL of DMEM medium to prepare a solution with concentration of 0.05 mg/m L. 500 µL 0.05 mg/mL solution was added with 500 µL of DMEM medium to prepare a solution with concentration of 0.025 mg/m L.

17
18

2. Positive Control Sample and Preparation of Administration Preparation:

Positive control sample: white or light yellow powder of chloroquine phosphate; 5 g; source: Bide Pharmaceutical; Article No.: BD263139-5g; and Batch No.: BNA684.

thawing again. 20 μL of supernatant was taken into 96-well full-white ELISA plate, and added with 100 μL of Luciferase Assay Reagent to detect luciferase activity (RLU, wherein high RLU value means more pseudoviruses entering the cell). The layout of the plate was as follows:

|  | 1 | 2 | 3 | 4 | 5 | 6 | 7 | 8 | 9 | 10 | 11 | 12 |
|---|---|---|---|---|---|---|---|---|---|---|---|---|
| A | 0 | 0 | 0 | 0 | 0 | 0 | 0 | 0 | 0 | 0 | 0 | 0 |
| B | 0 | HEK293 + | HEK293 + | HEK293 + | HEK293 + | HEK293 + | HEK293 + | medium | HEK293 + | 0 | 0 | 0 |
| C | 0 | drug-1 + | drug-2 + | drug-3 + | drug-4 + | drug-5 + | chloroquine |  | virus + | 0 | 0 | 0 |
| D | 0 | virus | virus | virus | virus | virus | phosphate + |  | DMSO | 0 | 0 | 0 |
|  |  |  |  |  |  |  | virus |  |  |  |  |  |
| E | 0 |  |  |  |  |  |  |  |  | 0 | 0 | 0 |
| F | 0 |  |  |  |  |  |  |  |  | 0 | 0 | 0 |
| G | 0 |  |  |  |  |  |  |  |  | 0 | 0 | 0 |
| H | 0 | 0 | 0 | 0 | 0 | 0 | 0 | 0 | 0 | 0 | 0 | 0 |

Preparation of administration preparation: 2.24 mg of chloroquine phosphate was weighed, added with 1.085 mL of DMEM, and mixed evenly to obtain a stock solution with a concentration of 4 mM; and 100 μL of mother liquor was added with 3900 μL of DMEM cell medium to prepare a solution with a concentration of 100 μM.

3. Cells for Test

Name or code: HEK293 cell line stably expressing ACE2 receptor.

Species source: human embryonic kidney cells; tissue source: normal renal cells; growth characteristics: adherent growth.

Medium: DMEM medium 90%; FBS, 10%.

4. Recombinant Novel Coronavirus for Test

Name: COVID-19 pseudovirus

Source: Guangzhou Paizhen Biotechnology Co., Ltd.

Batch No.: LV-nCov1-2

Production: pseudovirus system vector was used to produce pseudovirus in co-transfected multiple-plasmid mammalian cell system, thus producing infectious pseudovirus-like particles wrapped by pseudovirus capsid protein or envelope protein. Function is that the recombinant new coronal pseudovirus can be used to detect the invasiveness of pseudovirus in the test sample, which needs to be operated in the laboratory with level II biosafety.

5. Test Method:

D1, HEK293-ACE2 cells in logarithmic growth phase were adjusted to the cell concentration of $625 \times 10^4$ cells/m L, and cells were added into columns 2-7 and 9, and rows B-D of 96-well plate to 5000 cells/well/80 μL, and 80 μL of the newly formulated DMEM medium was added into column 8, and rows B-D, and cultivated overnight at 37° C. and 5% $CO_2$.

D2, the test sample group in columns 2-6, and rows B-D were added with 10 μL of the test sample with the concentration of 50 μg/mL, 20 μg/mL, 10 μg/mL, 5 μg/mL and 2.5 μg/mL in this order, and 10 μL of the pseudovirus liquid was added at the same time; the positive control group in column 7, and rows B-D added with 10 μL of chloroquine phosphate, and 10 μL of the pseudovirus liquid was added at the same time; the blank control group (column 8, rows B-D) was added with 20 μL of medium; the negative control group (column 9, rows B-D) was added with 10 μL of the pseudovirus liquid, containing 10 μL of solvent control with 0.25% DMSO. 40 μL of 1× Reporter Lysis Buffer was added after incubation at 37° C., and 5% $CO_2$ for 48 h, left at −80° C. for 2 h, and centrifuged at 4000 r/m in for 5 min after The results show that: after 48 h of drug action, RLU/RLUc value of positive control group (ratio of fluorescence value of test group to average fluorescence intensity of negative control group) was 0.05±0.01, and RLU/RLUc value of the test sample was 0.14±0.04, 0.09±0.03, 0.14±0.04, 0.11±0 01, and 0.17±0.14 in this order according to its concentration ranging from high to low (50 μg/mL, 20 μg/mL, 10 μg/mL, 5 μg/mL, and 2.5 μg/mL); compared with the negative control group, the RLU/RLUc value of each dosage group of the test sample was significantly different from that of the positive control group (* P<0.001; P<0.01). FIG. 7 shows the inhibitory effect of the Chinese traditional medicine extract on HEK293-ACE2 cells infected by COVID-19 pseudovirus.

The test shows: it can be seen from the above results that under the test condition, the above traditional Chinese medicine extracts have the inhibition rate of COVID-19 pseudovirus being more than 50% when their concentration is 2.5 μg/mL to 50 μg/mL, indicating that the traditional Chinese medicine extract H157 has a good inhibitory effect on COVID-19 pseudovirus infected HEK293 cell line stably expressing ACE2 receptor.

The Clinical Therapeutic Effect of the Traditional Chinese Medicine Composition of the Present Disclosure on Cold Dampness Diseases (i.e. Viral Pneumonia):

The traditional Chinese medicine composition prepared by the present disclosure was used for clinical test.

Object: patients in Danjiangkou Hospital of Traditional Chinese Medicine.

Case 1: Chen x, 13 years old, the imaging diagnosis report before treatment showed that: multiple patch-shaped density-increased opacity were seen in upper, middle, and lower lobe of right lung, and some of them showed ground glass changes; the result of novel coronavirus detection was negative; diagnosis: infectious virus in the right lung, considered as viral pneumonia. After the treatment of the traditional Chinese medicine composition of the present disclosure, the imaging diagnosis was that the infectious lesion of the right lung was more absorbed than before administration.

Case 2: Wang xx, 32 years old, the imaging diagnosis report before treatment showed that: the upper lobe of right lung and lower lobe of left lung had multiple patch-shaped and flake-shaped ground-glass density-increased opacity, and some lesions had consolidation, in which air broncho-gram sign can be seen, especially on the right upper lobe; the result of novel coronavirus detection was negative; diagnosis: infectious lesions in the upper lobe of the right lung and the lower lobe of the left lung, considered as viral pneumonia firstly. After the treatment of the traditional Chinese medicine composition of the present disclosure, the imaging diagnosis was that the infectious lesion of the upper lobe of right lung and lower lobe of left lung were more absorbed than before.

Case 3: Xie xx, 54 years old, the imaging diagnosis report before treatment showed that: there was patch-shaped density-increased opacity in the upper lobe of the right lung, with blurry edges, in which air bronchogram sign can be seen. The result of novel coronavirus detection was negative; diagnosis: infectious lesions in the right lower lung. After the treatment of the traditional Chinese medicine composition of the present disclosure, the imaging diagnosis was that the infective lesion of the right lower lung was better than before, and reexamination was recommended.

Case 4: A 17-year-old male was admitted to the hospital with fever for 3 days. Symptoms: fever and chills, dry cough, sore throat, body aches and hyperhidrosis. Imaging examination: right lower lung infection, possible viral pneumonia; etiological examination: negative result of novel coronavirus nucleic acid test. After being treated with the traditional Chinese medicine composition of the present disclosure, the patient had no fever and pharyngalgia, mitigated cough, and absorbed pulmonary inflammation.

Case 5: A 41-year-old male was admitted to the hospital with cough and expectoration for more than half a month. Symptoms: cough and expectoration. Imaging examination: right upper lung infection, possible viral pneumonia; etiological examination: negative result of novel coronavirus nucleic acid test. After being treated with the traditional Chinese medicine composition of the present disclosure for 14 days, the patient had no cough and expectoration, and showed the absorbed pulmonary inflammation. The treatment effect was remarkable.

Case 6: A 19-year-old male was admitted to the hospital with fever, shortness of breath and dizziness for 2 days. Symptoms: fever, lack of strength, dizziness, pharyngalgia and cough. Imaging examination: double lung infection, viral pneumonia with high possibility; etiological examination: negative result of novel coronavirus nucleic acid test. After being treated with the traditional Chinese medicine composition of the present disclosure for 3 days, the patient had no fever, mitigated cough and expectoration, improved strength and appetite, and showed the absorbed pulmonary inflammation. The treatment effect was remarkable.

Case 7: A 30-year-old female was admitted to the hospital with cough and expectoration for 3 days. Symptoms: cough, expectoration and dry pharynx. Imaging examination: right lower lung infection, possible viral pneumonia; etiological examination: negative result of novel coronavirus nucleic acid test. After being treated with the traditional Chinese medicine composition of the present disclosure for 4 days, the patient had mitigated cough and expectoration, improved dry pharynx, and showed the absorbed pulmonary inflammation. The treatment effect was remarkable.

Case 8: A 23-year-old male was admitted to the hospital with intermittent fever for 5 days. Symptoms: fever, aversion to cold, cough, poor appetite and poor sleep. Imaging examination: infection in lower lobe of left lung, possible viral pneumonia; etiological examination: negative result of novel coronavirus nucleic acid test. After being treated with the traditional Chinese medicine composition of the present disclosure for 7 days, the patient had no fever and aversion to cold, improved cough, and showed the absorbed pulmonary inflammation. The treatment effect was remarkable.

Case 9: A 31-year-old male was admitted to the hospital with fever for 15 days and chest distress and chest pain for 7 days. Symptoms: headache, poor appetite and lack of strength. Imaging examination: multiple infections of both lungs, possible viral pneumonia; etiological examination: negative result of novel coronavirus nucleic acid test. After being treated with the traditional Chinese medicine composition of the present disclosure for 6 days, the patient had no headache, improved poor appetite and lack of strength, and showed the absorbed pulmonary inflammation. The treatment effect was remarkable.

The traditional Chinese medicine composition of the present disclosure effectively relieves or treats viral pneumonia. After treatment, the chest imaging of the patient shows absorption of inflammation and recovery of lung function.

Finally, it should be noted that the above embodiments are only used to illustrate the technical solution of the present disclosure, not to limit it; although the present disclosure has been described in detail with reference to the aforementioned embodiments, those skilled in the art should understand that they can still modify the technical solutions recorded in the aforementioned embodiments, or equivalently replace some or all of the technical features therein. However, these modifications or substitutions do not make the nature of the corresponding technical solutions separate from the scope of the technical solutions of the embodiments of the present disclosure.

What is claimed is:

1. A method for treating Covid-19 associated pneumonia, wherein the method comprises administering therapeutically effective amount of the traditional Chinese medicine composition comprising in parts by weight: 250-400 parts of *Citri reticulatae pericarpium,* 100-200 parts of *Rhizoma Atractylodis,* 100-200 parts of *Cortex Magnoliae Officinalis,* 200-300 parts of *Radix Glycyrrhizae,* 200-300 parts of *Herba Agastaches,* 200-300 parts of *Acorus tatarinowii,* 250-330 parts of *Ziziphus jujuba Mill.,* and 100-200 parts of *Zingiber officinale Roscoe,* and a filler comprising dextrin, soluble starch, or lactose.

2. The method according to claim 1, wherein the traditional Chinese medicine composition comprises in parts by weight: 270-350 parts of *Citri reticulatae pericarpium,* 130-175 parts of *Rhizoma Atractylodis,* 130-175 parts of *Cortex Magnoliae Officinalis,* 200-260 parts of *Radix Glycyrrhizae,* 200-260 parts of *Herba Agastaches,* 200-260 parts of *Acorus tatarinowii,* 280-330 parts of *Ziziphus jujuba Mill.,* and 150-180 parts of *Zingiber officinale Roscoe,* and a filler comprising dextrin, soluble starch, or lactose.

3. The method according to claim 1, wherein the filler is present in an amount of 500-700 parts by weight.

4. The method according to claim 1, wherein the traditional Chinese medicine composition is an oral liquid, granule, pulvis, dropping pill, capsule, effervescing agent or tablet.

* * * * *